(12) United States Patent
Debrauwere et al.

(10) Patent No.: US 6,207,107 B1
(45) Date of Patent: Mar. 27, 2001

(54) STEAM STERILIZABLE SYSTEM FOR INACTIVATING VIRAL CONTAMINANTS IN BODY FLUIDS

(75) Inventors: Jack Debrauwere, Halle; Jean-Marie Mathias, Lillois, both of (BE); Indrajit Patel, Algonguin, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 07/952,427

(22) Filed: Oct. 5, 1992

(51) Int. Cl.$^7$ ................... A61L 2/07; A61L 2/08
(52) U.S. Cl. ................... 422/27; 422/22; 422/24
(58) Field of Search .................. 422/22, 24, 26–28, 422/32, 40, 41, 44, 905; 435/173.1, 173.3; 604/403, 408, 404, 416, 56, 83, 87, 89; 514/222.8

(56) References Cited

U.S. PATENT DOCUMENTS

| | | |
|---|---|---|
| 3,298,597 | 1/1967 | Bellamy, Jr. ................ 604/408 |
| 3,557,783 | 1/1971 | Castner ................... 604/20 |
| 4,119,267 | 10/1978 | Kydonieus ................ 604/408 |
| 4,212,299 | 7/1980 | Yokokoji et al. ........... 604/408 |
| 4,318,883 * | 3/1982 | Polony et al. ............. 422/22 |
| 4,402,318 | 9/1983 | Swartz ................... 604/20 |
| 4,453,940 | 6/1984 | Aoyagi et al. ............ 604/408 |
| 4,460,365 | 7/1984 | Ganshirt et al. .......... 604/408 |
| 4,596,657 | 6/1986 | Wisdom .................. 422/44 X |
| 4,748,120 | 5/1988 | Wiesehahn ............... 435/173.3 |
| 4,790,815 * | 12/1988 | Baldeau et al. ........... 604/408 X |
| 4,878,891 | 11/1989 | Judy et al. ............... 604/5 |
| 4,902,287 | 2/1990 | Carmen et al. ............ 604/416 |
| 4,906,103 | 3/1990 | Kao ..................... 604/404 X |
| 4,915,683 * | 4/1990 | Sieby ................... 604/416 X |
| 4,919,823 | 4/1990 | Wisdom ................. 422/41 X |
| 4,929,479 * | 5/1990 | Shishido et al. .......... 604/408 X |
| 4,950,665 * | 8/1990 | Floyd ................... 514/222.8 |
| 4,994,057 | 2/1991 | Carmen et al. ........... 604/416 |
| 5,066,290 * | 11/1991 | Measells et al. .......... 604/408 |
| 5,149,718 | 9/1992 | Mereulo et al. ........... 604/347 X |
| 5,196,001 | 3/1993 | Kao ..................... 604/416 |
| 5,226,564 | 7/1993 | Steer et al. .............. 604/317 X |
| 5,257,986 | 11/1993 | Herbert et al. ........... 604/416 |
| 5,263,925 | 11/1993 | Gilmore, Jr. et al. ....... 604/4 |
| 5,356,709 * | 10/1994 | Woo et al. ............... 428/376 |

FOREIGN PATENT DOCUMENTS

| | | |
|---|---|---|
| 39 30 510 A1 * | 3/1991 | (DE) . |
| 0 286 524 | 10/1988 | (EP) . |
| 0382 018 A2 | 8/1990 | (EP) . |
| WO 90/05548 | 5/1990 | (WO) . |
| WO 90/07876 | 7/1990 | (WO) . |
| WO 90/13296 | 11/1990 | (WO) . |

OTHER PUBLICATIONS

Bernd Lambrecht, et al., "Photoinactivation of Viruses in Human Fresh Plasma by Phenothiazine Dyes in Combination with Visible Light", Vox Sang 1991:60:207–213.

* cited by examiner

Primary Examiner—Robert J. Warden, Sr.
Assistant Examiner—Theresa T. Snider
(74) Attorney, Agent, or Firm—Robert M. Barrett; Bradford R. L. Price; Amy L. H. Rockwell

(57) ABSTRACT

A steam sterilizable unit for inactivating pathogens in a body fluid is provided including a plastic structure for housing a therapeutically effective amount of a methylene blue solution. The plastic structure preferably includes at least an inner layer constructed from a non-PVC plastic. Preferably, the methylene blue solution has a pH of less than 7.0 and preferably less than or equal to approximately 6.3.

10 Claims, 1 Drawing Sheet

STEAM STERILIZABLE SYSTEM FOR INACTIVATING VIRAL CONTAMINANTS IN BODY FLUIDS

BACKGROUND OF THE INVENTION

The present invention relates generally to systems, for collecting and housing body fluids. More specifically, the present invention relates to apparatus and methods for housing body fluids and solutions for inactivating viral contaminants that may be present in the body fluids.

In a variety of therapies, such as transfusions and transplants, body fluids, especially blood components such as red blood cells, platelets, plasma, leukocytes, and bone marrow, are infused from one or more individuals into a patient. Although such therapies provide treatments, some of which are life saving, and cannot otherwise be provided, due to the transmission of infectious diseases there may be potential risks involved with such therapies.

By way of example, it is known that blood can carry infectious agents such as hepatitis virus, human immunodeficiency virus (an etiological agent for AIDS), and herpes virus. Although screening methods exist to identify blood that may include such viruses, blood containing viruses, and other disease causing pathogens, such as bacteria, cannot be 100% eliminated from the pool of possible blood component supplies. Therefore, there is still a small risk that blood transfusions can transmit viral or other infections.

Accordingly, a goal of recent biomedical research has been to reduce the risk of transmitting an infectious agent by selectively inactivating or depleting pathogens present in such blood components. One approach has been to utilize photosensitive (photoactive) agents that when activated by light of the appropriate wavelength will destroy the ability of the pathogen to cause infection. The use of photodynamic therapy has been suggested as a way to eradicate infectious agents from collected blood and its components prior to storage and/or transfusion.

A number of different photoactive agents have been proposed as possibilities to be used to eradicate viral and other contaminants in body fluids. Such photoactive agents include: psoralens; porphyrins; phthalocyanines; and dyes such as methylene blue. See, for example, U.S. Pat. Nos. 4,748,120; 4,878,891; 5,120,649; and German Patent Application No. DE 39 30 510 A1 (Mohr).

Although much effort has been focussed on commercializing such methods using photoactive agents, the inventors believe that such methods are currently not commercial. Even though a commercial system for utilizing a photoactive agent to treat blood to eradicate or remove viral and other contaminants has not been developed, it is envisioned that such a system would entail combining the blood with the photoactive agent in a container and irradiating the resultant mixture with light of the appropriate wavelength.

It is known, of course, to use blood pack units to collect blood. The blood pack units include a container typically constructed from a plastic material, usually a polyvinyl chloride material. The blood pack units are connected to tubes that allow blood to be infused into the container as well as to be accessed therefrom.

Of course, blood pack units must be sterilized. Typically, sterilization takes place by steam sterilization at a temperature of above 100° C. for a predetermined period of time.

One photoactive agent that appears to be promising with respect to eradicating viruses and bacteria from blood is methylene blue. Methylene blue, 3-7-bis(dimethylamino) phenothiazine-5-ium chloride, ($C_{16}H_{18}ClN_3S$), in the presence of light has been reported to damage DNA. Accordingly, it can be used to selectively, in a controlled manner, modify the DNA and RNA of bacterial and viral contaminants thereby inactivating the pathogens. See U.S. Pat. No. 4,950,665.

It has recently been determined, however, that if methylene blue is placed into a standard blood pack unit constructed from PVC under standard conditions and the unit is then sterilized, that at least a certain amount of the methylene blue migrates into the PVC layer reducing the methylene blue present. The specific amount of methylene blue that migrates is variable depending upon the conditions. However, envisioned methods of using methylene blue to treat blood and other body fluids require that precise amounts of methylene blue be used.

This unfortunately requires that the blood packs must be sterilized prior to methylene blue being added thereto. This can create logistical problems, as well as increase the cost of creating the product. Likewise, during the methylene blue filling process, there is the risk of contaminating the sterilized container.

SUMMARY OF THE INVENTION

Applicants have surprisingly discovered that methylene blue can be housed in certain containers, or under certain conditions, and sterilized with the blood pack unit without the methylene blue migrating into the plastic. It has been found that two of the parameters that have a great effect on preventing methylene blue from migrating into the plastic are: the type of plastic; and the pH of the methylene blue solution.

It has been surprisingly found that methylene blue does not migrate into non-PVC material as well as into PVC material under sterilization conditions. Accordingly, in one embodiment of the invention, the present invention provides a steam sterilizable housing that includes a therapeutically effective amount of methylene blue in a solution. The housing includes at least an inner surface, the surface that contacts the methylene blue solution, that is constructed from a non-PVC material.

In an embodiment, the housing is a container of a blood pack unit that is designed to receive blood or a blood component.

The housing can also be a steam sterilizable tube including a therapeutically effective amount of a viral inactivating agent for use in blood therapy. The tube defines an interior having a first and a second end. These ends are initially closed. The interior is defined by an inner surface constructed from a non-PVC material. The interior includes therein a therapeutically effective amount of methylene blue.

In an embodiment, the tube is constructed from a monolayer material. In a further embodiment of the invention, the tube is constructed from a multi-layer material. In a preferred embodiment of such a multi-layer layer tube, the outer layer of the tube is sealable to a PVC material.

In another embodiment of the present invention, a therapeutically effective methylene blue solution is provided. The methylene blue solution is adjusted to a pH of less than 7.0 and preferably, approximately 6.3 or less and is designed to be housed in a plastic container that will e be sterilized.

In another embodiment of the invention, a steam sterilizable unit for inactivating pathogens in a body fluid is provided comprising a plastic structure housing a therapeutically effective amount of a methylene blue solution having a pH of less than 7.0 and preferably less than or equal to approximately 6.3.

In an embodiment, the plastic structure is a container designed to house blood or a blood component.

In an embodiment, the plastic structure is a tube that is coupled to a container designed to house blood or a blood component.

The present invention also provides methods for inactivating pathogens that may be present in a body fluid.

An advantage of the present invention is that a blood pack unit can be provided that includes a viral inactivating agent therein.

A further advantage of the present invention is that it provides a container including a viral inactivating agent that can be steam sterilized.

Furthermore, an advantage of the present invention is that a sterilizable tubing, that can be sealed to a PVC container, can be provided that includes a therapeutically effective amount of methylene blue.

Still further, an advantage of the present invention is to provide an improved method for inactivating pathogens that may be contained in a body fluid.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

Figure 1:
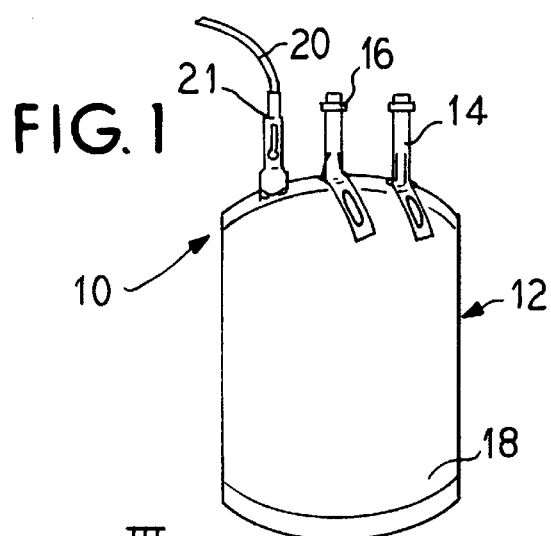
FIG. 1 illustrates an embodiment of a blood pack unit constructed pursuant to the present invention.

The present invention relates to apparatus and methods for containing body fluids and/or inactivating pathogens that may be contained in the body fluids. As used herein, body fluid not only includes blood and its components, but also includes other fluids contained in the body or fluid containing structures such as, e.g., bone marrow, semen, and internal organs.

As previously noted, although body fluids, such as blood and its components, can be used in many therapeutic applications, there is the danger of the transfer of infectious disease due to viral and bacterial contaminants that may be contained in such fluids. Recently the use of photoactive agents has provided the hope of inactivating viral and bacterial contaminants that may be contained in such fluids. However, in order to commercialize such methods, certain obstacles must be overcome.

It is known to house blood components in plastic containers. Typically, the plastic container comprises a polyvinyl chloride structure that is plasticized with di(2-ethylhexyl)phthalate (DEHP) and includes stabilizers. It has been found that when a solution of methylene blue, a photoinactive agent of promise, is placed in such a container at a physiological pH of around 7, that upon steam sterilization, the photoinactive agent (methylene blue) migrates into the plastic.

Methods of use of methylene blue to inactivate viral contaminants require rather precise amounts of methylene blue. See, for example, Lambrecht et al, *Photoinactivation of Viruses in Human Fresh Plasma by Phenothiazine Dyes in Combination with Visible Light*, Vox Sang 1991; 60:207–213. Therefore, the migration of the methylene blue solution into the plastic during the sterilization process provides an unacceptable system.

The inventors have surprisingly found that the migration of methylene blue into the plastic is dependent on a couple of controllable parameters. Therefore, pursuant to the present invention, it is possible to provide apparatus and systems wherein methylene blue can be contained within a plastic structure, the structure can be steam sterilized, and the methylene blue solution will be recovered in sufficient quantity to allow the solution to be used to inactivate viral contaminants in a body fluid.

For example, in an embodiment of the present invention, the inventors have found that by controlling the type of plastic from which the housing that contains the methylene blue is constructed, that the migration of methylene blue into the housing can be controlled. In this regard, it has been found that if at least the layer of the container that contacts the methylene blue is constructed from a non-PVC material, the methylene blue stored therein will not substantially migrate into the plastic.

Although it is envisioned that with proper controls of other parameters, any non-PVC plastic material can be used, of most interest are the more inert plastics, such as polyolefins and polyurethanes. In a preferred embodiment, polypropylene, styrene-ethylene-butylene-styrene (SEBS), ethylene vinyl acetate, and polyesters are used.

By way of example, referring now to FIG. 1, a blood pack unit 10 is illustrated. The blood pack unit includes a container 12 having ports 14 and 16 extending therefrom to provide access to an interior 18 of the container. Additionally, a tubing 20 extends from the container. The tubing 20 can be used to infuse a body fluid such as whole blood or a blood component into the container 12.

In the blood pack unit 10 illustrated, the tubing 20 extends from the container 12 and provides means for infusing blood or blood components into the blood pack. An example of a system that can be used is the Optipak® system that is disclosed in U.S. Pat. No. 4,608,178. In this system, plasma or red blood cells, for example, can be infused into the container 12 through the tubing 20 after having been separated from whole blood.

The container 12 can have a structure that is substantially similar to the container for housing blood and blood components available from the Fenwal Division of Baxter International Inc. However, preferably, the container 12 is constructed so that at least an interior layer that defines the interior surface of the container is constructed from a non-PVC material. Most preferably, at least the inner surface of the container 12 is constructed from SEBS, polypropylene, polyester, polyurethane, or ethylenevinyl acetate, or blends thereof. Of course, if desired, the entire container 12 can be constructed from a non-PVC material.

Pursuant to the present invention, the container 12 includes a quantity of methylene blue. In a preferred embodiment that has been found to function satisfactorily, the container contains 10 ml of a methylene blue solution. As set forth in the experiments disclosed below, it has been found that the pH of the solution can effect the migration of the solution into the plastic material during sterilization. Preferably, the methylene blue solution has been adjusted to a pH of less than 7.0 and most preferably approximately 6.3 or less.

Pursuant to the present invention, the methylene blue solution is infused into the container 12 of the blood pack unit 10. The blood pack unit 10 including container 12 and methylene blue solution can then be steam sterilized, e.g., at 115° C. for 65 minutes. Due to the use of a methylene blue solution having a pH of less than 7.0 and the fact that the container 12 includes at least an inner surface that is constructed from a non-PVC material, the methylene blue solution, during steam sterilization, will not substantially migrate into the plastic.

A body fluid, such as a blood component, can then be infused into the container 12 through tubing 20. To control fluid flow through the tubing 20, a breakable cannula 21 or other means can be used.

In the container 12, the blood component will mix with the methylene blue solution. The container 12 is then irradiated by light of the appropriate wavelength (approximately 620–670 nm) to activate the methylene blue within the container 12. This will cause the methylene blue to inactivate any pathogens, e.g. viruses and bacteria, that are contained within the blood component, thus insuring a blood component that does not contain pathogens.

Figure 2:
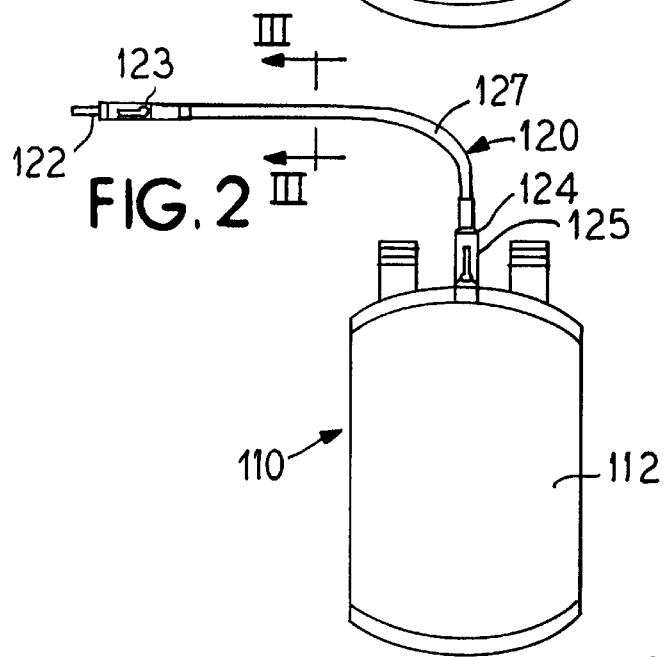
FIG. 2 illustrates a further embodiment of a blood pack unit constructed pursuant to the present invention.

In a further embodiment of the present invention illustrated in FIG. 2, the methylene blue is contained within a coextruded tubing 120 that is connected to the container 112. The tubing 120 is closed at each of a first and second end 122 and 124, respectively. The tubing 120 can be closed using breakable cannulas 123 and 125 that allow fluid flow after being manipulated, or other means.

Preferably, the tube 120 is constructed from a material having at least an inner layer, that defines the interior 127, that is constructed from a non-PVC material. In this regard, the tubing 120 can be constructed from a monolayer or a multi-layer material.

If a monolayer materials is used, preferably, it is a non-PVC material. Most preferably, the monolayer material is solvent sealable to PVC allowing the tube 120 to be sealed to a standard PVC container. Polyurethane will function satisfactorily for this application. It can be sealed to PVC with cyclohexanone. Additionally, it is sealable using radio frequency (a Hematron) allowing the tube to be sealed after being used to allow blood to be infused into the container.

Figure 3:
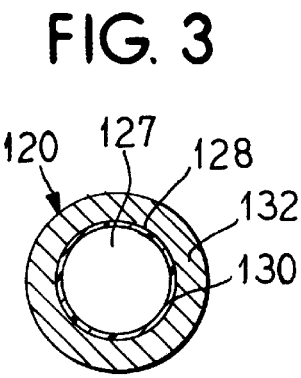
FIG. 3 illustrates a cross-sectional view of the tube of FIG. 2 taken along lines III—III.

Referring to FIG. 3, an embodiment of the present invention is illustrated wherein a multi-layer material is used. In the preferred embodiment illustrated, the inner layer 128 is constructed from a non-PVC material. In an embodiment that has been found to function satisfactorily, the inner layer 128 is constructed from a blend of approximately: 60% SEBS; 20% polypropylene; and 20% ethylenevinyl acetate The middle layer 130 is constructed from a blend of approximately 50% SEBS; 38% polyester; 10% EVA; and 2% polypropylene. The middle layer 130 functions as a tie layer. The outer layer 132 is constructed from a PVC material to allow the tube 120 to be sealed to a standard PVC container 112. In an embodiment, the outer layer is constructed from PVC, DEHP, and stabilizers. Due to the middle layer 130, the inner layer 128 and outer layer 132 are secured together.

In an embodiment, the tube 120 can be a two layer coextruded tube. The interior layer is non-PVC and the outer layer is sealable to PVC, for example, PVC. An example of a structure that has been found to function satisfactorily is an inner layer of a blend of: SEBS; polyester; polyvinyl acetate; and polypropylene, and an outer layer of: PVC; DEHP; and stabilizers. Preferably, the outside to inside layer thickness ratio is approximately 9:1.

As in the previous embodiment illustrated in FIG. 1, preferably, 10 ml of methylene blue solution is contained with the tube 120. Likewise, preferably the solution has a pH of approximately 6.3 or less.

During manufacture, the tube 120 containing the methylene blue solution is steam sterilized at 115° C. for 65 minutes along with the blood pack 110. The blood pack unit 110 can then be utilized to inactivate any pathogens contained in a body fluid. To this end, to infuse blood into the container, the breakable cannulas 123 and 125 are broken allowing blood to flow through the tubing 120. As the blood flows through the tubing 120 it flows through the methylene blue solution mixing therewith. This mixture flows into the container 112.

Once in the container 112, the methylene blue solution and blood are completely mixed and then irradiated with light of the appropriate wavelength to activate the photoactive agent. The activated methylene blue will thereby inactivate any pathogens that may be contained within the blood.

Figure 4:
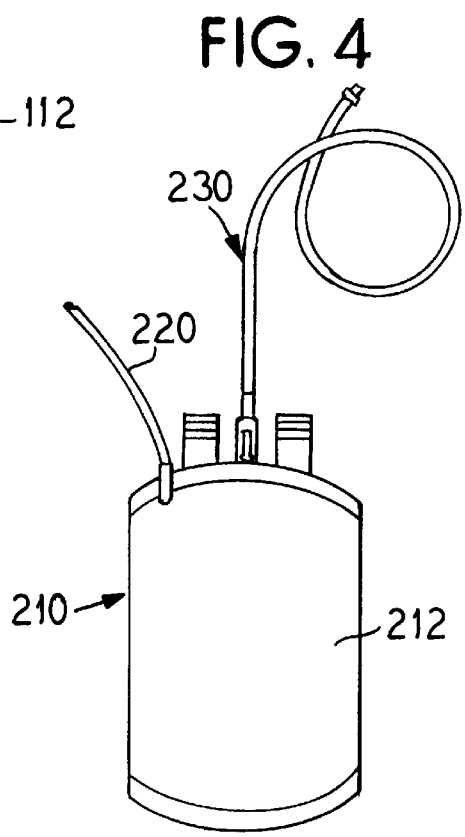
FIG. 4 illustrates a further embodiment of a blood pack unit constructed pursuant to the present invention.

FIG. 4 illustrates a further embodiment of a blood pack unit 210. As illustrated, the unit 210 includes a container 212. A tubing 220 provides fluid communication from a body fluid source to the container 210.

A further tube 230 includes a solution of methylene blue. The tube 230 can be constructed in accordance with the principles discussed with respect to the embodiment of the tubing 120 set forth above. In use, after, during, or before a body fluid is infused into the container 212, the methylene blue solution is communicated into the container by stripping the tube 230. The container 212 and body fluid/methylene blue solution are then irradiated.

By way of example and not limitation, examples of the present invention will now be given.

EXAMPLE NO. 1

Three containers constructed from different PVC materials were tested to determine recovery of the methylene blue.

To this end, a solution of methylene blue was made by dissolving 50 mg of methylene blue into a liter of citrate buffer solution, pH 4.0. A 50 ppm resultant solution was created. This solution was then diluted 5 times with the same citrate buffer solution, pH 4.0, to obtain a solution of 10 ppm.

Another solution of methylene blue was made by dissolving 50 mg of methylene blue into a liter of phosphate buffer solution, pH 7.5. A 50 ppm resultant solution was created. This solution was then diluted 5 times with the same phosphate buffer solution, pH 7.5, to obtain a solution of 10 ppm. To each type of PVC plastic container were added either 10 ml of the pH 4.0 methylene blue solution or 10 ml of the pH 7.5 methylene blue solution.

Each container was then steam sterilized at 115° C. for 65 minutes. The methylene blue present in each container was then measured to determine the percent of recovery after sterilization.

It was found that the highest methylene blue recovery was obtained with the type 1 PVC plastic container (81%) filled with 10 ml of methylene blue solution buffered at pH 4.0. It was also found that virtually all the methylene blue had migrated inside any of the PVC plastic container when the solution was buffered at pH 7.5.

TABLE 1

Effect of pH of the MB Solution
and Type of PVC Plastic Container

| | Container | | |
|---|---|---|---|
| pH | 1 | 2 | 3 |
| 4.0 | 81 | 80 | 67 |
| 7.5 | 1.5 | 0 | 0 |

% of MB Recovery After Sterilization.
Container Material:
1 - PVC; DEHP; and Stabilizers.
2 - PVC; TEHTM; and Stabilizers.
3 - PVC; N-butyl, Tri-N-hexyl, Citrate; and Stabilizers.

EXAMPLE NO. 2

It has been found that just a pH adjustment (no use of any buffer) of the methylene blue can have an effect on the percent recovery of the methylene blue after sterilization of a PVC plastic container. In this regard, the following experiments were conducted.

The effect of the pH of the methylene blue solution of Example 1 set forth above was considered.

The 10 ppm methylene blue solution was prepared in two steps—by dissolving 50 mg of methylene blue into a liter of distilled water followed by dilution 5 times of this 50 ppm solution with distilled water to obtain a solution of 10 ppm.

The pH was adjusted at various levels utilizing 0.1 N hydrochloric acid.

To a plastic blood bag container constructed from polyvinyl chloride, di(2-ethylhexyl)phthalate (DEHP—a plasticizer), and stabilizers was added 10 ml of the methylene blue solution adjusted at 4 different levels of pH. Each container was then steam sterilized at 115° C. for 65 minutes. The percent of methylene blue recovery was measured after sterilization.

TABLE 2

In this table, the effect of pH range of methylene blue solution for a given PVC container made from PVC, DEHP, and stabilizers was considered. The methylene blue solution was made as set forth in Example 1 except the pH was adjusted using 0.1 n HCl as indicated.

| pH | % of MB Recovery after sterilization |
|---|---|
| 3.0 | 95 |
| 4.0 | 88 |
| 5.0 | 78 |
| 6.3 | 81 |

EXAMPLE NO. 3

The effect of plastic material (PVC and non-PVC container) for a given pH of the methylene blue solution (pH=4.0) was considered. As set forth in the Table below, two containers were compared:

a plastic blood bag container constructed from polyvinyl chloride, tri(2-ethylhexyl)trimellitate (TEHTM—a plasticizer), and stabilizers; and a blood bag container constructed from a blend of approximately 60% SEBS, 20% polypropylene, and 20% ethylenevinyl acetate (the non-PVC container).

Each container was filled with 10 ml of the methylene blue solution, pH 4.0 of Example No. 2. The containers were then steam sterilized at 115° C. for 65 minutes. The percent of recovery of methylene blue was then measured.

It was found that in the PVC container, only 81% of the methylene blue was recovered after sterilization. In contrast, however, in the non-PVC container, 96% of the methylene blue was recovered after sterilization. 96% recovery of the methylene blue is sufficiently high to provide a viable system.

| Container | % of MB Recovery after sterilization |
|---|---|
| A | 81 |
| B | 96 |

Container Material:
A - PVC; TEHTM; and Stabilizers.
B - A blend of approximately 60% SEBS, 20% PP, and 20% EVA.

In view of the experiments set forth in the above examples, in an embodiment of the present invention, the pH of the methylene blue solution is adjusted to insure that it is less than 7.0 and preferably equal to or less than approximately 6.3.

EXAMPLE NO. 4

Additionally, the effect of aging has been considered using methylene blue and a non-PVC container. Accelerated stability studies have shown that a 10 ml methylene blue solution, made in accordance with Example No. 2, in a container made from a blend of approximately 60% SEBS, 20% PP, 20% EVA and overwrapped in an aluminum foil (protection from daylight exposure) did not degrade after 6-month storage at 45° C.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for storing a body fluid and inactivating pathogens contained therein comprising the steps of:

providing a container for receiving a body fluid; including an interior portion defined by inner walls constructed from a non-PVC material;

placing an effective amount of a methylene blue solution having a pH of less than about 7.0 to substantially inactivate any pathogens present in a body fluid added to the interior portion of the container, in the interior of the container;

steam sterilizing the container;

transferring body fluid into the interior of the container; and irradiating the container with light to activate the methylene blue solution and inactivate pathogens present in the body fluid.

2. The method of claim 1 wherein the methylene blue solution has a pH of less than or equal to 6.3.

3. A method for inactivating pathogens that may be present in a body fluid comprising the steps of:

providing a system including a container for receiving a body fluid and a tube connecting the container with a source of body fluid;

locating within the system an effective amount of a methylene blue solution having a pH of less than 7.0 to substantially inactivate any pathogens present in a body fluid added to the container;

steam sterilizing the system;

transferring a body fluid into the container through the tube and causing the body fluid to mix with the methylene blue solution; and irradiating a resultant body fluid/methylene blue solution with light to inactivate pathogens contained therein.

4. The method of claim 3 including the step of:

initially locating the methylene blue in the tube of the system.

5. The method of claim 3 including the step of:

initially locating the methylene blue in the container of the system.

6. The method of claim 3 including the step of:

providing the tube with an inner surface constructed from a non-PVC material.

7. The method of claim 3 including the step of:

providing the container with an interior constructed from a non-PVC material.

8. The method of claim 3 including the step of providing the system with a second tube that initially houses the methylene blue solution.

9. A steam sterilizable container for use in a system for inactivating viruses comprising:

a container having an inner sidewall surface defining a fluid-receiving interior portion, the inner sidewall surface being constructed of a non-PVC plastic material including a blend of styrene-ethylene-butylene-styrene, polypropylene and ethylene vinyl acetate; and an effective amount of a methylene blue solution viral inactivation agent having a pH of less than or equal to 6.3 to substantially inactivate any pathogens present in a body fluid added to the container, disposed in the interior portion, and the container containing the methylene blue solution being steam sterilized prior to use.

10. A method for providing a controlled amount of methylene blue viral inactivation agent in a steam sterilizable container adapted to receive a body fluid for use in a system for inactivating viruses comprising the steps of:

providing a desired amount of a methylene blue solution having a pH of less than or equal to 6.3; and adding the methylene blue solution to an interior portion of a steam sterilizable container having an inner contact surface constructed of a non-PVC plastic material, so that migration of the methylene blue agent into the plastic of the container upon steam sterilization is reduced or eliminated and the desired viral inactivating amount of methylene blue is provided when body fluids are added to the interior, the container containing the methylene blue solution being steam sterilized prior to use.

* * * * *